(12) United States Patent
Salin

(10) Patent No.: US 10,146,946 B2
(45) Date of Patent: Dec. 4, 2018

(54) METHOD OF RESTORING SETTINGS OF AN INSTRUMENT FOR PROCESSING A SAMPLE OR A REAGENT AND A SYSTEM FOR PROCESSING A SAMPLE OR REAGENT

(71) Applicant: Roche Diagnostics Operations, Inc., Indianapolis, IN (US)

(72) Inventor: Richard Edward Salin, Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 35 days.

(21) Appl. No.: 15/379,934

(22) Filed: Dec. 15, 2016

(65) Prior Publication Data

US 2017/0177880 A1     Jun. 22, 2017

(30) Foreign Application Priority Data

Dec. 18, 2015   (EP) .................................... 15201311

(51) Int. Cl.
*G06F 11/14*     (2006.01)
*G06F 21/60*     (2013.01)
(Continued)

(52) U.S. Cl.
CPC ..... *G06F 21/602* (2013.01); *G01N 35/00584* (2013.01); *G01N 35/00613* (2013.01); *G01N 35/00712* (2013.01); *G01N 35/00732* (2013.01); *G06F 8/65* (2013.01); *G06F 9/4401* (2013.01); *G06F 9/45512* (2013.01); *G06F 11/00* (2013.01); *G06F 11/1448* (2013.01); *G06F 11/1464* (2013.01); *G06F 11/1469* (2013.01);
(Continued)

(58) Field of Classification Search
CPC ..................... G06F 11/1448; G06F 11/1469
See application file for complete search history.

(56) References Cited

U.S. PATENT DOCUMENTS 7,565,544 B1   7/2009   Eatough et al.
7,797,285 B1   9/2010   Rivera et al.
(Continued)

FOREIGN PATENT DOCUMENTS

EP   1275222 B1   10/2011
EP   2674887 A1   12/2013

*Primary Examiner* — Albert Wang
(74) *Attorney, Agent, or Firm* — Roche Diagnostics Operations, Inc.

(57) ABSTRACT

A method for saving and/or restoring settings of an instrument for processing a sample or reagent is disclosed. The instrument comprises a control unit and an operating system. A storage medium is provided to the instrument. The storage medium comprises a script. The script restores data for restoring settings of the instrument. The script is encrypted and/or digitally signed. The method verifies an identity and/or integrity of the script and executes the script upon starting the instrument by the operating system with the storage medium when the identity and/or integrity of the script correspond to an identity and/or integrity of the instrument. The control unit provides an input menu for allowing a user to input a saving and/or restoring command. The instrument saves settings on the storage medium and/or restores settings of the instrument from the storage medium by the restoring data corresponding to the saving and/or restoring command.

17 Claims, 2 Drawing Sheets

(51) Int. Cl.
*G16H 10/60* (2018.01)
*G01N 35/00* (2006.01)
*G06F 8/65* (2018.01)
*G06F 11/00* (2006.01)
*G06F 21/51* (2013.01)
*G06F 9/4401* (2018.01)
*H04L 9/32* (2006.01)
*G06F 9/455* (2018.01)
*G06F 19/00* (2018.01)
*G06F 21/57* (2013.01)
*G06F 21/64* (2013.01)

(52) U.S. Cl.
CPC .............. *G06F 19/00* (2013.01); *G06F 21/51* (2013.01); *G06F 21/572* (2013.01); *G06F 21/575* (2013.01); *G06F 21/64* (2013.01); *G16H 10/60* (2018.01); *H04L 9/3247* (2013.01)

(56) References Cited

U.S. PATENT DOCUMENTS

| | | | |
|---|---|---|---|
| 2008/0262776 A1* | 10/2008 | Yamasaki | G16H 10/40 702/108 |
| 2009/0167871 A1 | 7/2009 | Usui | |
| 2009/0286484 A1* | 11/2009 | Phung | H04L 41/00 455/67.11 |
| 2011/0289497 A1 | 11/2011 | Kiaie et al. | |
| 2014/0005951 A1 | 1/2014 | Werner et al. | |
| 2014/0370609 A1 | 12/2014 | Frank et al. | |
| 2015/0067342 A1 | 3/2015 | Pazdziora et al. | |

* cited by examiner

METHOD OF RESTORING SETTINGS OF AN INSTRUMENT FOR PROCESSING A SAMPLE OR A REAGENT AND A SYSTEM FOR PROCESSING A SAMPLE OR REAGENT

CROSS-REFERENCE TO RELATED APPLICATIONS

This application claims priority to EP 15201311.6, filed Dec. 18, 2015, which is hereby incorporated by reference.

BACKGROUND

The present disclosure generally relates to a method for restoring settings of an instrument for processing a sample or reagent and a system comprising an instrument for processing a sample or reagent and a storage medium.

In vitro diagnostic testing has a major effect on clinical decisions by providing physicians with pivotal information. Particularly, there is great emphasis on providing quick and accurate test results in critical care settings. In vitro diagnostic testing is usually performed using instruments operable to execute one or more processing steps/workflow steps on one or more biological samples and/or one or more reagents, such as pre-analytical instruments, post-analytical instruments and also analytical instruments.

Analytical instruments/analyzers are configured to obtain a measurement value. An analyzer is operable to determine via various chemical, biological, physical, optical or other technical procedures a parameter value of the sample or a component thereof. An analyzer may be operable to measure the parameter of the sample, or of at least one analyte, and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzer are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

In order to ensure proper operation of the instruments and a way to restore setting of the instrument in case of a malfunction/defect, restoring data for restoring settings of the instrument are stored on a storage medium communicatively connected to the instrument. This is usually performed in a so-called backup operation carried out regularly.

Known instruments are configured to receive a storage medium with restoring data and to recover the instrument settings therefrom. One known solution is that the instrument software is provided with a feature to read the restoring data and restore the instrument settings accordingly. However, there are cases when the instrument software itself becomes inoperable and/or inaccessible so that even the feature to recover the instrument settings is unavailable and/or unreliable.

In order to address such cases, prior art instruments are known which are configured to receive a bootable recovery media and boot up the instrument from said bootable recovery media, the latter comprising functionality to recover the instrument settings.

However, configuring an instrument to accept bootable recovery media and boot therefrom introduces major security vulnerability as it leaves open the option to boot from malicious bootable media. For example such malicious bootable media comprises software code which is designed to circumvent the data protection and/or the authentication-authorization mechanisms of the instrument.

Therefore, there is a need for an efficient, flexible and secure backup procedure of an apparatus for processing a sample or reagent, particularly of an off-line apparatus, such as a medical device, in case of a system failure.

SUMMARY

According to the present disclosure, a system and method for restoring settings of an instrument for processing a sample or reagent are presented. The instrument can comprise a control unit and an operating system. The method can comprise providing a storage medium. The storage medium can comprise a script and restoring data for restoring settings of the instrument. The script can be encrypted/digitally signed. The instrument can receive the storage medium. The method can further comprise verifying an identity and/or integrity of the script, executing the script upon starting the instrument by the operating system with the storage medium received by the instrument when the identity and/or integrity of the script corresponds to an identity of the instrument, providing an input menu by the control unit for allowing a user to input a saving and/or restoring command, and saving settings of the instrument on the storage medium and/or restoring settings of the instrument from the storage medium by the restoring data corresponding to the saving and/or restoring command.

Accordingly, it is a feature of the embodiments of the present disclosure to provide an efficient, flexible and secure backup procedure of an apparatus for processing a sample or reagent, particularly of an off-line apparatus, such as a medical device, in case of a system failure. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
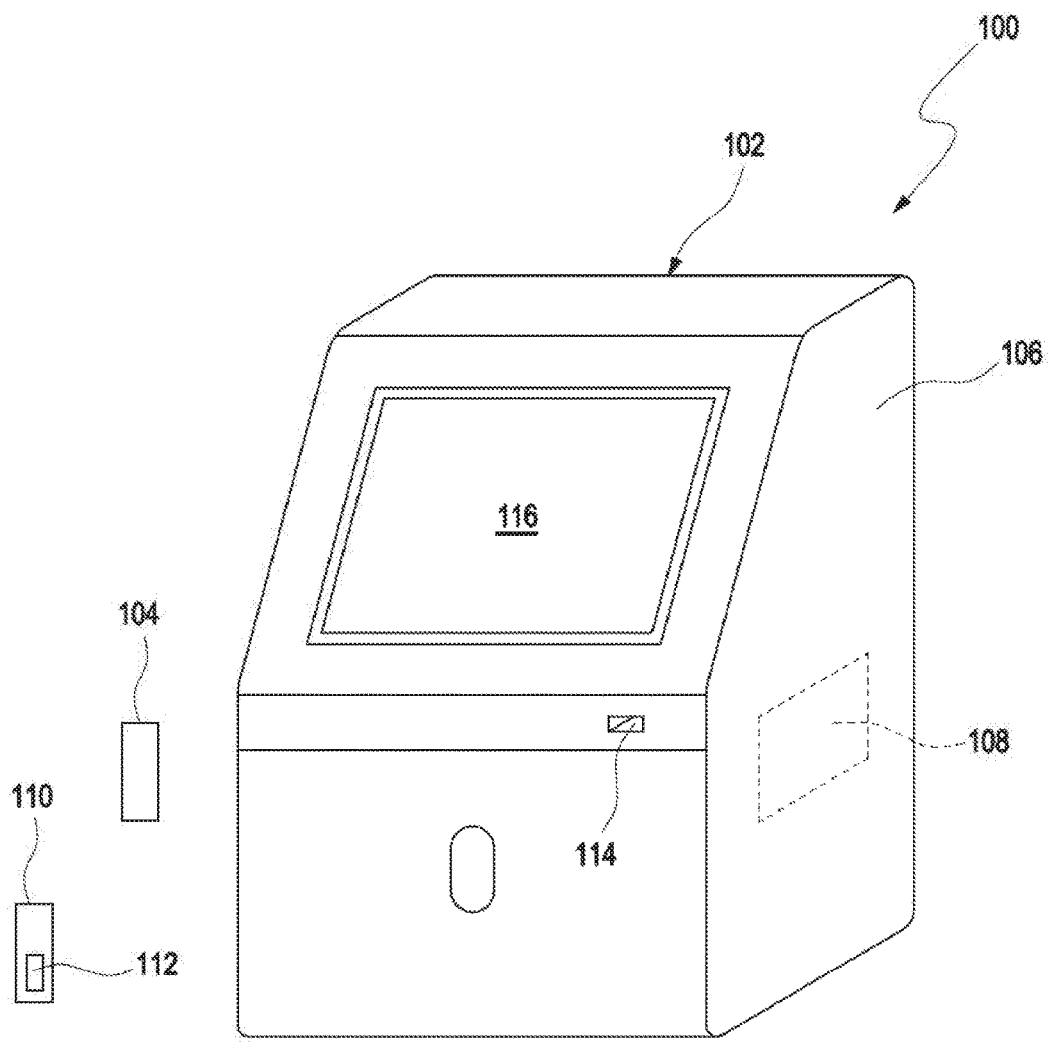
FIG. 1 illustrates a perspective view of a system comprising an instrument for processing a sample or a reagent and a storage medium according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Embodiments of the disclosed method and system aim to provide a safe and reliable way for restoring settings of an instrument.

Disclosed herein are a method for restoring settings of an apparatus for processing a sample or reagent and a system comprising an apparatus for processing a sample or reagent and a storage medium that provide an efficient, flexible and secure backup procedure of an apparatus for processing a sample or reagent, particularly of an off-line apparatus, such as a medical device, in case of a system failure.

As used in the following, the terms "have", "comprise" or "include" or any arbitrary grammatical variations thereof can be used in a non-exclusive way. Thus, these terms may both refer to a situation in which, besides the feature introduced by these terms, no further features can be present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically can be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "particularly", "more particularly", "specifically", "more specifically" or similar terms are used in conjunction with additional/alternative features, without restricting alternative possibilities. Thus, features introduced by these terms are additional/alternative features and are not intended to restrict the scope of the claims in any way. The invention may, as the skilled person will recognize, be performed by using alternative features. Similarly, features introduced by "in an embodiment of the invention" or similar expressions are intended to be additional/alternative features, without any restriction regarding alternative embodiments of the invention, without any restrictions regarding the scope of the invention and without any restriction regarding the possibility of combining the features introduced in such way with other additional/alternative or non-additional/alternative features of the invention.

According to the disclosed method/system, a method for restoring settings of an instrument for processing a sample or reagent is disclosed. The instrument can comprise a control unit and an operating system. A storage medium can be provided. The storage medium can comprise a script. The storage medium can also comprise restoring data for restoring settings of the instrument. The script can be encrypted and/or digitally signed. The instrument can receive the storage medium. An identity and/or integrity of the script can be verified. The script can be executed when the identity and/or integrity of the script corresponds to an identity and/or integrity of the instrument. The script can be executed upon starting the instrument by the operating system with the storage medium received by the instrument. An input menu can be provided by the control unit for allowing a user to input a saving and/or restoring command. The settings of the instrument can be saved on the storage medium and/or the settings of the instrument can be restored from the storage medium by the restoring data corresponding to the saving and/or restoring command. In other words, the settings of the instrument can be saved on the storage medium and/or the settings of the instrument can be restored from the storage medium by the restoring data dependent on whether the saving and/or restoring command has been input.

The term "instrument" as used herein can refer to any apparatus, or apparatus component, operable to execute one or more processing steps/workflow steps on one or more biological samples and/or one or more reagents. The expression 'processing steps' thereby can refer to physically executed processing steps such as centrifugation, aliquotation, sample analysis and the like. The term 'instrument' can cover pre-analytical instruments, post-analytical instruments and also analytical instruments. Thus, the term "instrument" can be used synonymous with the term "laboratory instrument."

The term 'analyzer'/'analytical instrument' as used herein can encompass any apparatus, or apparatus component, configured to obtain a measurement value. An analyzer can be operable to determine via various chemical, biological, physical, optical or other technical procedures, a parameter value of the sample, or a component thereof. An analyzer may be operable to measure the parameter of the sample, or of at least one analyte, and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzer are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term "script" as used herein can refer to a program written in a scripting language and that can be written so that the operating system of the instrument can interpret and execute the instructions of the script. By contrast, normal programs are typically written in a compiled language and distributed in machine code form. Due to the nature of the script, modifications can be introduced with very little effort whereas a program based approach can require more significant changes and recompilation of the software. A script can therefore be a list of instructions to be executed.

The term 'control unit' as used herein can encompass any physical or virtual processing device configurable to control a laboratory instrument, or system, comprising one or more laboratory instruments in a way that workflow(s) and workflow step(s) can be conducted by the laboratory instrument/system. The control unit may, for example, instruct the laboratory instrument/system to conduct pre-analytical, post analytical and analytical workflow(s)/workflow step(s). The control unit may receive information from a data management unit regarding which steps need to be performed with a certain sample. In some embodiments, the control unit may be integral with a data management unit, may be comprised by a server computer and/or be part of one laboratory instrument or even distributed across multiple instruments of the laboratory system. The control unit may, for instance, be embodied as a programmable logic controller running a computer-readable program provided with instructions to perform operations.

As mentioned above, the method can include a step of verifying an identity of the script. This step as used herein can refer to a part of an authentication process of the script. Authentication can be the act of confirming the truth of an attribute of a single piece of data claimed true by an entity. In the disclosed method/system, authentication can involve verifying the validity of identification of the script. In other words, the operating system can compare information concerning allowable scripts stored on the instrument with information given by the script. If the comparison reveals a match of information, authenticity of the script can be verified, i.e., proofed. In this case, the script can be allowed to be executed.

Alternatively, or in addition, the method can include a step of verifying an integrity of the script. This step as used herein can refer to a part of a process for checking of completeness and/or intactness. With this process, data of the script can be checked which have been stored on the storage medium beforehand by a comparison based on redundancy such as a checksum added to reference data. Such a checksum may be a digital signature. If this check reveals that the script is complete and intact, the script can be allowed to be executed.

The term "settings" as used herein can refer to a configuration of the instrument, i.e., an arrangement of functional units according to their nature, number, and chief characteristics. The configuration can affect the function and performance of the instrument and can include at least instructions according to which the instrument acts.

The method can provide flexibility and security as using a script instead of a software based approach can provide platform and device type independence. This can mean it can be run on an arm, x86, power pc, and the like without the need to distribute different versions. Further, as the script is encrypted and/or digitally signed, security of the data transmission can be provided. Particularly, the script may be password free and data transmission can still be secured as the script can only be executed if the identity and/or integrity of the script is verified. Furthermore, a backup can be created at any time, even after a failure of the instrument when the normal software doesn't boot, as long as the instrument hardware is healthy.

In one embodiment, the storage medium may not be bootable. The term "bootable" as used herein can refer to a device that can be booted. Analogously, the term "not bootable" can indicate the avoiding of a bootable drive to prevent any operating system to be booted. The term 'boot' as used herein can refer to an initialization of a computerized system from a switched-off state. Booting typically involves performing a power-on self-test, locating and initializing peripheral device, and then finding, loading and starting an operating system A storage medium being not bootable can remove the risk of using a malicious bootable medium to access the data. It can allow a simple identification of the authenticity of the stick using signing.

The script may be encrypted by a signature. Thus, a simple identification of the authenticity of the storage medium may be provided using signing.

The method may further comprise decrypting the script when the identity and/or integrity of the script correspond to the identity and/or integrity of the instrument. Thus, the script cannot be viewed nor changed due to encryption but only after decryption.

Restoring settings of the instrument from the storage medium may include copying the restoring data from the storage medium to the instrument. Thus, a full data backup or update can be allowed which can be particularly relevant for debugging purposes wherein an issue could be caused due to unknown data.

Restoring of settings of the instrument from the storage medium may include decrypting the restoring data from the storage medium. Thus, it can be ensured that the restoring data can be only copied to the instrument if the identity and/or integrity of the script corresponds to the identity and/or integrity of the instrument as only in this case the restoring data are decrypted. Thus, security of the restoring data can be increased.

Saving settings of the instrument may include copying settings data on the storage medium. Thus, backup data may be generated and the settings may be duplicated.

Saving settings of the instrument on the storage medium may include encrypting settings data on the storage medium. Thus, the settings can be securely stored.

The settings of the instrument may be stored in a database. Saving settings may include copying the database on the storage medium. Thus, a generation of full backup data can be possible contrary to using a compact flash card, wherein only a partial backup data generation can be possible.

The database may be compressed before being copied on the storage medium. Thus, the data amount may be reduced. The database may be protected by a password. Thus, the script cannot be viewed nor changed due to encryption. The password may be created by the operating system. Thus, a simple way of protecting the settings data can be provided.

Starting the instrument may include booting the instrument. Booting the instrument may include detecting whether the storage medium is received by the instrument. Thus, normal booting of the instrument can include looking for the script. Booting the instrument may be disabled when the script is executed. Thus, normal booting of the instrument from a storage medium can be disabled but the boot sequence of the instrument can look for the script and can allow the same to be executed.

The storage medium may be given an identification number which can be logged. Thus, logging all data extractions can be provided.

Restoring settings of the instrument may include inputting of a password by a user. Thus, restoring, or updating, of the settings can be only carried out if an operator, or user, is inclined to do so.

The instrument may comprise a display device. The input menu may be provided on the display device. Thus, a user friendly handling of the script can be provided. The input menu may be configured to allow a user to exit the input menu without inputting the saving and/or restoring command. The instrument can be booted in case of an exit of the input menu. Thus, execution of the script may be prevented by the user of the instrument in order to allow booting of the instrument.

The storage medium may be an USB storage device such as, for example, an USB stick. Thus, a common storage device may be used to store the script. Accordingly, as USB connection devices are common to most instrument in the field of the disclosed method/system, the method may be carried out with almost every instrument in the field of the disclosed method/system.

Further, according to the disclosed method/system, a system comprising an instrument for processing a sample or reagent is disclosed. The instrument can comprise a control unit and an operating system. The system can further comprise a storage medium. The storage medium can comprise a script. The script can comprise restoring data for restoring settings of the instrument. The instrument can be configured to carry out each step of the method as described above.

The instrument may comprise a connection device configured to receive the storage medium. Thus, the connection device can allow a user to insert the storage medium into the instrument. The operating system may be configured to start the instrument with the storage medium received by the instrument. The script may be encrypted and/or digitally signed. The operating system may be configured to verify an identity and/or integrity of the script. The instrument may be configured to execute the script in case the identity and/or integrity of the script corresponds to an identity and/or integrity of the instrument. The control unit may be configured to provide an input menu for allowing a user to input a saving and/or restoring command. Further, the instrument may be configured to save settings of the instrument on the storage medium and/or to restore settings of the instrument from the storage medium by the restoring data corresponding to or dependent on the saving and/or restoring command.

Thus, the system can provide flexibility and security as using a script instead of a software based approach can provides platform and device type independence. This can mean it can be run on an arm, x86, power pc and the like without the need to distribute different versions. Further, as the script can be encrypted and/or digitally signed, security of the data transmission can be provided. Particularly, the script may be password free and data transmission can still be secured as the script can only be executed if the identity and/or integrity of the script is verified.

Furthermore, a backup can be created at any time, even after a failure of the instrument when the normal software doesn't boot, as long as the instrument hardware is healthy.

The storage medium may not be bootable. A storage medium not being bootable can remove the risk of using a malicious bootable medium to access the data. It can allow a simple identification of the authenticity of the stick using signing.

The script may be encrypted by a signature. Thus, a simple identification of the authenticity of the storage medium may be provided using signing.

The operating system may be configured to decrypt the script when the identity and/or integrity of the script correspond to the identity and/or integrity of the instrument. Thus, the script cannot be viewed nor changed due to encryption but only after decryption.

The operating system may be configured to copy the restoring data from the storage medium to the instrument for restoring settings of the instrument from the storage medium. Thus, the system can allow a full data backup or update which can be particularly relevant for debugging purposes wherein an issue could be caused due to unknown data.

The operating system may be configured to decrypt the restoring data from the storage medium for restoring settings of the instrument from the storage medium. Thus, it can be ensured that the restoring data can only be copied to the instrument if the identity and/or integrity of the script correspond to the identity and/or integrity of the instrument as only in this case the restoring data are decrypted. Thus, security of the restoring data can be increased.

The operating system may be configured to copy settings data on the storage medium for saving settings of the instrument on the storage medium. Thus, backup data may be generated and the settings may be duplicated. The operating system may be configured to encrypt settings data on the storage medium for saving settings of the instrument on the storage medium. Thus, system can allow the settings to be securely stored.

The instrument may be configured to store the settings in a database. The operating system may be configured to copy the database on the storage medium for saving the settings. Thus, a generation of full backup data can be possible. The operating system may be configured to compress the database before being copied on the storage medium. Thus, the data amount may be reduced.

The instrument may be configured to protect the database by a password. Thus, the script cannot be viewed nor changed due to encryption. The operating system may be configured to create the password. Thus, a simple way of protecting the settings data can be provided.

The operating system may be configured to boot the instrument for starting of the instrument. The operating system may be configured to detect whether the storage medium is received by the instrument during booting of the instrument. Thus, instrument can look for the script during normal booting.

Booting the instrument may be disabled when the script is executed. Thus, normal booting of the instrument from a storage medium can be disabled but the boot sequence of the instrument can look for the script and allow the same to be executed.

The storage medium may be given an identification number which can be logged. Thus, logging all data extractions can be provided.

The control unit may be configured to require inputting of a password by a user for restoring settings of the instrument. Thus, restoring or updating of the settings can only be carried out if a user is inclined to do so.

The storage medium may be a USB storage device such as, for example, an USB stick. Thus, a common storage device may be used to store the script. Accordingly, as USB connection devices are common to most instruments in the field of the disclosed method/system, the method may be carried out with almost every instrument in the field of the disclosed method/system.

The instrument may comprise a display device. The control unit can be configured to provide the input menu on the display device. Thus, a user friendly handling of the script can be provided.

The input menu may be configured to allow a user to exit the input menu without inputting the saving and/or restoring command. The operating system can be configured to boot the instrument in case of an exit of the input menu. Thus, execution of the script may be prevented by the user of the instrument in order to allow booting of the instrument.

A computer script is also presents and can include computer-executable instructions for performing the method according to the disclosed method/system in one or more of the embodiments enclosed herein when the script is executed on a computer or computer network. Specifically, the computer script may be stored on a computer-readable data carrier. Thus, specifically, one, more than one or even all of the method steps as indicated above may be performed by using a computer, or a computer network, in particular by using a computer script.

A computer script product having script code is also presented to perform the method according to the disclosed method/system in one or more of the embodiments enclosed herein when the script can be executed on a computer, or computer network. Specifically, the script code may be stored on a computer-readable data carrier.

Further, a data carrier having a data structure stored thereon is presented which, after loading into a computer or computer network, such as, for example, into a working memory or main memory of the computer, or computer network, may execute the method according to one or more of the embodiments disclosed herein.

A computer script product with script code stored on a machine-readable carrier is presented; in order to perform the method according to one or more of the embodiments disclosed herein, when the script can be executed on a computer, or computer network. As used herein, a computer script product can refer to the script as a tradable product. The product may generally exist in an arbitrary format, such as in a paper format, or on a computer-readable data carrier. Specifically, the computer script product may be distributed over a data network.

Finally, a modulated data signal is presented which can contain instructions readable by a computer system, or computer network, for performing the method according to one or more of the embodiments disclosed herein.

Referring to the computer-implemented aspects, one or more of the method steps or even all of the method steps of the method according to one or more of the embodiments disclosed herein may be performed by using a computer, or computer network. Thus, generally, any of the method steps including provision and/or manipulation of data may be performed by using a computer, or computer network. Generally, these method steps may include any of the method steps, typically except for method steps requiring manual work, such as providing the samples and/or certain aspects of performing the actual measurements.

Specifically, the disclosed method/system further discloses:

a computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer script, wherein the computer script is adapted to perform the method according to one of the embodiments described in this description while the script is being executed on a computer, a computer script comprising a script for performing the method according to one of the embodiments described in this description while the computer script is being executed on a computer or on a computer network, a computer script comprising a script according to the preceding embodiment, wherein the script is stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer script product having script code, wherein the script code can be stored or is stored on a storage medium, for performing the method according to one of the embodiments described in this description, if the script code is executed on a computer or on a computer network.

Summarizing the findings of the disclosed method/system, the following embodiments are disclosed:

A method for restoring settings of an instrument for processing a sample or reagent is presented. The instrument can comprise a control unit and an operating system. The method can comprise providing a storage medium. The storage medium can comprise a script. The script can comprise restoring data for restoring settings of the instrument. The script can be encrypted/digitally signed. The instrument can receive the storage medium. The method can further comprise verifying an identity and/or integrity of the script, executing the script upon starting the instrument by the operating system with the storage medium received by the instrument when the identity and/or integrity of the script corresponds to an identity and/or integrity of the instrument, providing an input menu by the control unit for allowing a user to input a restoring command, and saving settings of the instrument on the storage medium and/or restoring settings of the instrument from the storage medium by the restoring data corresponding to the restoring command.

The storage medium may not be bootable.

The script can be encrypted by a signature.

The method can further comprise decrypting the script when the identity of the script corresponds to the identity of the instrument.

Restoring settings of the instrument from the storage medium can include copying the restoring data from the storage medium to the instrument.

Restoring settings of the instrument from the storage medium can include decrypting the restoring data from the storage medium.

Saving settings of the instrument on the storage medium can include copying settings data on the storage medium.

Saving settings of the instrument on the storage medium can include encrypting settings data on the storage medium.

The settings of the instrument can be stored in a database. Saving setting can include copying the database on the storage medium. The database can be compressed before being copied on the storage medium. The database can be protected by a password. The password can be created by the operating system.

Starting of the instrument can include booting the instrument. Booting the instrument can include detecting whether the storage medium is inserted into the instrument. Booting the instrument can be disabled when the script is executed.

The storage medium can be given an identification number which can be logged.

Restoring settings of the instrument can include inputting a password by a user.

The storage medium can be an USB storage device.

The instrument can comprise a display device. The input menu can be provided on the display device. The input menu can be configured to allow a user to exit the input menu without inputting the restoring command. The instrument can be booted in case of an exit of the input menu.

A system comprising an instrument for processing a sample or reagent is presented. The instrument can comprise a control unit, an operating system, and a storage medium. The storage medium can comprise a script. The script can comprise restoring data for restoring settings of the instrument. The instrument can be configured to carry out the above method. The instrument can comprise a connection device configured to allow the storage medium to be inserted into the instrument. The operating system can be configured to start the instrument with the storage medium inserted into the instrument and to execute the script. The control unit can be configured to provide an input menu for allowing a user to input a saving and/or restoring command. The instrument can be configured to save settings of the instrument on the storage medium and/or to restore settings of the instrument from the storage medium by the restoring data corresponding to the saving and/or restoring command.

The operating system can be configured to decrypt the script when the identity of the script corresponds to the identity of the instrument.

The operating system can be configured to copy the restoring data from the storage medium to the instrument for restoring settings of the instrument from the storage medium.

The operating system can be configured to decrypt the restoring data from the storage medium for restoring settings of the instrument from the storage medium.

The operating system can be configured to copy settings data on the storage medium for saving settings of the instrument on the storage medium.

The operating system can be configured to encrypt settings data on the storage medium for saving settings of the instrument on the storage medium.

The instrument can be configured to store the settings in a database. The operating system can be configured to copy the database on the storage medium for saving the settings. The operating system can be configured to compress the database before being copied on the storage medium. The instrument can be configured to protect the database by a password. The operating system can be configured to create the password.

The operating system can be configured to boot the instrument for starting of the instrument. The operating system can be configured detect whether the storage medium is inserted into the instrument during booting of the instrument. Booting the instrument can be disabled when the script is executed.

The control unit can be configured to require inputting of a password by a user for restoring settings of the instrument.

Referring initially to FIG. 1, FIG. 1 shows a perspective view of a system 100 comprising an instrument 102 for processing a sample 104 or reagent. The instrument 102 can comprise a control unit 106 and an operating system 108. The control unit 106 may be a commercially available PC or the like on which the operating system 108 can run. The system 100 can further comprise a non-bootable storage medium 110. The storage medium 110 may be a USB stick or the like. The storage medium 110 may be given an identification number which can be logged. The storage medium 110 can comprise a script 112. The script 112 can comprise restoring data for restoring settings of the instrument 102. The script 112 can be encrypted. Alternatively, or in addition, the script 112 may be digitally signed. In one embodiment, the script 112 can be encrypted by a signature.

The instrument 102 can further comprise a connection device 114 configured to receive the storage medium 110. The connection device 114 can allow a user to insert the storage medium 110 into the instrument 102. For example, the connection device 114 may be an USB slot. The instrument 102 can further comprise a display device 116. The display device 116 may be a monitor. The display device 116 may comprise a graphical user interface such as a touch screen for allowing a user to communicate with the instrument 102 by inputting commands and instructions, respectively.

The instrument 102 may also be called a laboratory instrument. For example, the instrument 102 can be an analyzer, or analytical instrument. As such, the analyzer can be configured to obtain a measurement value form the sample 104. The analyzer can be operable to determine a parameter value of the sample 104, or a component thereof. For example, the analyzer can be configured to be used as point of care testing.

The term "point of care testing" as used herein can encompass analysis of one or more patient sample(s) at or near the site of patient care, i.e., a healthcare setting where medical, or medically related services, can be provided, such as emergency departments, intensive care units; primary care setting; medical centers, and the like. Point of care testing can often be accomplished through the use of transportable, portable, and handheld instruments, but small bench analyzers or fixed equipment can also be used when a handheld device is not available. The goal can be to collect the patient sample and obtain the analytical data in a very short period of time at or near the location of the patient. For example, the patient may be a human person, the sample may be human blood and the analyzer may be configured to detect blood glucose value as measuring data.

Thus, the instrument 102 can be configured to obtain measuring data from the sample 104. The so obtained measuring data can be stored in the control unit 106. The instrument 102 can be configured to carry out the analyzing process according to the settings thereof. Needless to say, the settings of the instrument 102 can comprise further or other data for operating the instrument 102. The settings may be stored in a database of the instrument 102. The database may be protected by a password created by the operating system 108.

Figure 2:
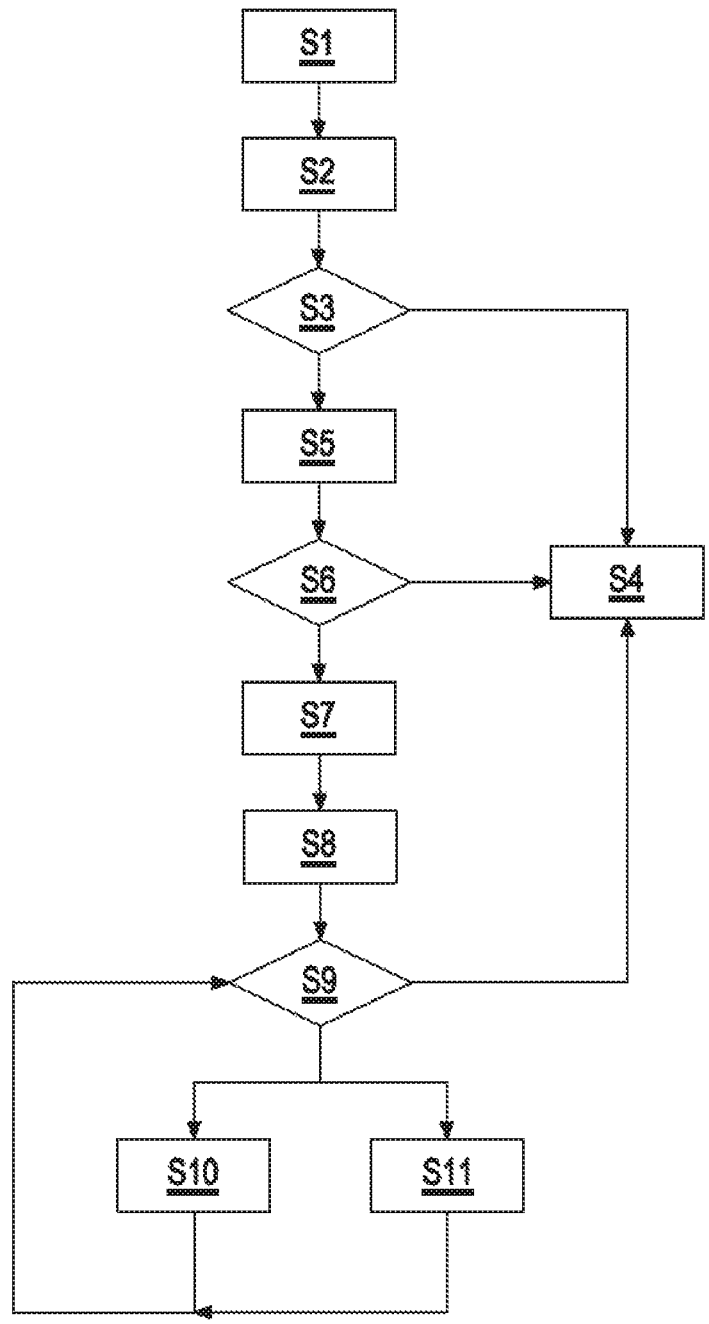
FIG. 2 illustrates a flowchart of a method according to the disclosed method/system according to an embodiment of the present disclosure.

FIG. 2 shows a flow chart of a method for saving and/or restoring settings of the instrument 102. Basically, each of the method steps described below may be carried out by the instrument 102. In step S1, the instrument 102 can be started by the operating system 108. In step S2, the operating system 102 can begin to boot and to launch a storage medium detection script. In other words, when the instrument 102 is booted, it can begin to execute a storage medium script for detecting a receipt of the storage medium 110. In step S3, the operating system 108 can detect whether the storage medium 110 is inserted into or received by the instrument 102 and the connection device 114, respectively.

If the storage medium 110 is not received by the instrument 102, the method can proceed to step S4. The instrument 102 can be regularly, or normally, booted. In the case, the storage medium 110 is detected, the method can proceed to step S5. The storage medium 110 can be received by the instrument 102 and the connection device 114, respectively. In step S6, the operating system 108 can verify an identity and/or integrity of the script 112. In other words, the operating system 108 can check whether a correctly named and encrypted script file is found on the storage medium 110. If the identity and/or integrity of the script 112 does not correspond to an identity and/or integrity of the instrument 102, i.e., the script 112 is not the correct one, the method can returns to step S4. i.e., the instrument 102 can be booted normally. If the identity and/or integrity of the script 112 correspond to an identity and/or integrity of the instrument 102, i.e. the script 112 is the correct one, the method can proceed to step S7, wherein the script 112 can be decrypted and executed by the operating system 108. When the script 112 is executed, booting of the instrument 102 can be disabled. The instrument 102 cannot be booted from the storage medium 110 as it is a non-bootable storage medium 110.

Subsequently, the method can proceed to step S8, wherein the control unit 106 can provide an input menu on the display device 116. The user may input commands within the input menu by the graphical user interface of the display device 116. The input menu can allow a user to make a selection. More particularly, the user may select between three options inputted in step S9. As a first option, the user may exit the input menu without inputting any other command other than an exit command. In this case, the method can proceed to step S4. As a second option, the input menu can allows the user to input a saving command. As a third option, the input menu can allow the user to input a restoring command. If the user inputs a saving command in step S9, the method can proceed to step S10, wherein the settings data can be copied from the instrument 102 to the storage medium 110 by the operating system 108 for saving settings of the instrument 102. More particularly, the operating system 108 can copy the database, in which the settings can be stored, on the storage medium 110. The operating system 108 may compress the database before being copied on the storage medium 110. The settings data may be encrypted. For example, the instrument 102 may protect the database by a password created by the operating system 108. Subsequently, the method can return to step S9.

If the user inputs a restoring command in step S9, the method can proceed to step S11, wherein the restoring data can be copied from the storage medium 110 to the instrument 102. More particularly, the control unit 106 can require inputting of a password by a user for restoring settings of the instrument 102 in order to decrypt the restoring data for restoring settings of the instrument 102 from the storage medium 110. Then the settings of the instrument 102 can be restored. The restoring process may also include an update process. Subsequently, the method can return to step S9.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for restoring settings of an instrument for processing a sample or reagent, wherein the instrument comprises a control unit and an operating system, the method comprises:
    providing a storage medium, wherein the storage medium comprises a script and restoring data for restoring settings of the instrument, wherein the script is encrypted/digitally signed and wherein the instrument receives the storage medium;
    verifying an identity and/or integrity of the script;
    decrypting the script when the identity and/or integrity of the script corresponds to the identity and/or integrity of the instrument;
    executing the script upon starting the instrument by the operating system with the storage medium received by the instrument when the identity and/or integrity of the script corresponds to an identity of the instrument;
    providing an input menu by the control unit for allowing a user to input a saving and/or restoring command; and
    saving settings of the instrument on the storage medium and/or restoring settings of the instrument from the storage medium by the restoring data corresponding to the saving and/or restoring command.

2. The method according to claim 1, wherein the storage medium is not bootable.

3. The method according to claim 1, wherein restoring settings of the instrument from the storage medium includes copying and decrypting the restoring data from the storage medium to the instrument.

4. The method according to claim 1, wherein the saving of settings of the instrument on the storage medium includes copying and encrypting settings data on the storage medium.

5. The method according to claim 1, wherein the settings of the instrument are stored in a database.

6. The method according to claim 5, wherein the saving of settings includes copying the database on the storage medium, and wherein the database is compressed before being copied on the storage medium.

7. The method according to claim 6, wherein the database is compressed before being copied on the storage medium.

8. The method according to claim 1, wherein the starting of the instrument includes booting of the instrument.

9. The method according to claim 8, wherein the booting of the instrument includes detecting whether the storage medium is inserted into the instrument.

10. The method according to claim 8, wherein the booting of the instrument is disabled when the script is executed.

11. A system, the system comprising:
    an instrument for processing a sample or reagent and a storage medium, wherein the instrument comprises:
    a control unit, and
    an operating system, wherein the storage medium comprises a script, wherein the script comprises restoring data for restoring settings of the instrument, wherein the script is encrypted and/or digitally signed,
    wherein the instrument is configured to carry out the method according to claim 1.

12. The system according to claim 11, wherein the instrument further comprises,
    a connection device configured to allow the storage medium to be received by the instrument, wherein the operating system is configured to:
    start the instrument with the storage medium received by the instrument, verify an identity and/or integrity of the script,
execute the script when the identity and/or integrity of the script corresponds to an identity and/or integrity of the instrument;
wherein the control unit is configured to provide an input menu for allowing a user to input a saving and/or restoring command; and
wherein the instrument is configured to save settings of the instrument on the storage medium and/or to restore settings of the instrument from the storage medium by the restoring data corresponding to the saving and/or restoring command.

13. The system according to claim 12, wherein the instrument comprises a display device, wherein control unit is configured to provide the input menu on the display device.

14. The system according to claim 11, wherein the storage medium is not bootable.

15. The system according to claim 11, wherein the operating system is configured to decrypt the script when the identity of the script corresponds to the identity of the instrument.

16. The system according to claim 11, wherein the operating system is configured to copy and decrypt the restoring data from the storage medium to the instrument for restoring settings of the instrument from the storage medium.

17. The system according to claim 11, wherein the operating system is configured to copy and encrypt settings data on the storage medium for saving settings of the instrument on the storage medium.

* * * * *